US006799731B2

(12) United States Patent
Marcacci

(10) Patent No.: US 6,799,731 B2
(45) Date of Patent: Oct. 5, 2004

(54) SCULPTING CLAY APPLICATOR

(76) Inventor: Philip Marcacci, 6368 Jadeite, Alta Loma, CA (US) 91737

( * ) Notice: Subject to any disclaimer, the term of this patent is extended or adjusted under 35 U.S.C. 154(b) by 0 days.

(21) Appl. No.: 10/256,414

(22) Filed: Sep. 27, 2002

(65) Prior Publication Data

US 2004/0144856 A1 Jul. 29, 2004

(51) Int. Cl.[7] .............................. B05B 1/24; B05B 7/32; A61M 11/02; F23D 11/24

(52) U.S. Cl. ........................ 239/128; 239/139; 239/337; 239/373

(58) Field of Search ................................ 239/128, 135, 239/139, 337, 373

(56) References Cited

U.S. PATENT DOCUMENTS 2,123,604 A * 7/1938 Johnson ....................... 239/127
2,335,123 A * 11/1943 Kinnard ....................... 425/96
2,579,357 A * 12/1951 Arvelund ..................... 239/79
2,642,643 A * 6/1953 Montague ................ 425/376.1
2,686,695 A * 8/1954 Kelly et al. ................. 239/127
2,762,901 A * 9/1956 Liedberg .................... 392/481
2,817,600 A * 12/1957 Yahnke ...................... 427/180
3,812,226 A * 5/1974 De Bussy ...................... 264/6
4,657,794 A * 4/1987 Schultze et al. ........... 428/34.5
4,812,428 A * 3/1989 Kohut ........................ 501/148
5,090,617 A * 2/1992 Swan et al. .................... 236/3
6,302,334 B1 * 10/2001 Restrepo ..................... 239/139
6,446,878 B1 * 9/2002 Chandra et al. ............... 239/1

OTHER PUBLICATIONS

U.S. Pat. No. 6,010,655, issued on Jan. 4, 2000, and entitled "Method of Making a Ceramic Ornament Having Short Undercuts on Surface thereof" to Chen.

U.S. Pat. No. 5,942,261, issued Aug. 24, 1999, and entitled "Handheld Modeling Tool" to Dreith.

U.S. Pat. No. 5,763,102, issued on Jun. 9, 1998, and entitled "Method of Making an Intaglio Three–Dimensional Solid Sculpture"issued to Yau.

U.S. Pat. No. 5,693,369, issued on Dec. 2, 1997, and entitled "Process for Finishing a Bronze Sculpture" issued to Russell.

U.S. Pat. No. 5,690,231, issued on Nov. 25, 1997, and entitled "Clay Sculpturing Kit" issued to Erickson.

U.S. Pat. No. 5,585,123, issued on Dec. 17, 1996, and entitled "Sculpting Tool" issued to Busby.

U.S. Pat. No. 4,659,319, issued on Apr. 21, 1987, and entitled "Image in Three Dimension with Picture Covering and Forming System" issued to Blair.

* cited by examiner

*Primary Examiner*—William C. Doerrler
(74) *Attorney, Agent, or Firm*—Mark Ogram

(57) ABSTRACT

An applicator for clay or wax which is brought to a liquid state using a heating vessel. The heating vessel uses boiling water to properly heat a pressure vessel in which the solid clay or wax has been placed. The insides of the pressure vessel is pressurized so that the liquidified material is passed through a heated hose to be applied by the operator using a nozzle at the end of the hose.

20 Claims, 5 Drawing Sheets

SCULPTING CLAY APPLICATOR

BACKGROUND OF THE INVENTION

This invention relates generally to sculpting and more specifically to the application of clay, wax, or similar material to a mold or foam for final sculpting.

The use of clay for art goes back at least to 27,000 B.C. and the introduction of sun-dried clay artifacts. Even from around 11,000 B.C. fired clay objects have been found.

Clay remains one of the fundamental materials used in art work In the modem realm, clay's ability to be easily molded and shaped often make it the material of choice for many artists. The clay is often sculpted into the art work which is then bronzed or used for a mold to make other statuettes.

In one technique, an original sculpture call a "machette" of the art work is enlarged using styra-foam. A thin layer of clay or wax is then added to the foam enlargement. This quarter to half inch of clay provides a-base for the artist to create the finer details of the sculpture.

Clay, although being pliable, is difficult to apply to the foam. The process can become very labor intensive and often "dulls" the outline of the foam.

It is clear there is a need for a faster and more controlled application of clay to an enlargement

SUMMARY OF THE INVENTION

While the following discussion relates to the invention's application to solid clay, the invention is not so limited and is intended to include solid wax and other materials which are clear to those of ordinary skill in the am The invention utilizes an applicator for clay or wax which is brought to a liquid state using a heating vessel. In this context, the heating vessel has an open top and is heated using electrical, gas, or another method.

Water is maintained within the heating vessel. This water is brought to the boiling point and is used to provide consistent heat over the surface of a pressure vessel contained within the heating vessel.

Solid clay or wax is deposited in the pressure vessel and is sealed therein. The boiling water, at 100 degrees Celsius, heats the pressure vessel such that the solid clay or wax is melted into a liquid state. In this context, "liquid" refers to the condition in which the clay or wax flows into the shape of its container.

During the heating process, the pressure vessel is sealed to obtain a more efficient heating of the clay or wax and also to provide the mechanism for the proper dispensing of the wax or clay once it becomes liquid.

The insides of the pressure vessel is pressurized. A standpipe within the pressure vessel communicates with a hose/handle assembly. The pressure within the pressure vessel forces the liquidified material through the standpipe and into the hose/spray gun.

The operator/artist uses the handle, equipped with a nozzle, to selectively spray the liquid clay/wax onto the foam to the desired depth. As the clay/wax leaves the nozzle, it is subjected to the ambient conditions and solidifies quickly after being applied to the machette.

In this manner, the operator/artist is able to apply a coating of clay or WAY to the foam at the desired depth Once the clay has solidified on the foam, then the artist is able to sculpt the desired image.

The invention, together with various embodiments thereof, will be more fully explained by the accompanying drawings and the following description thereof.

DRAWINGS IN BRIEF

FIGS. 1A and 1B graphically illustrate the operation of the preferred embodiment of the invention.

Figure 4:
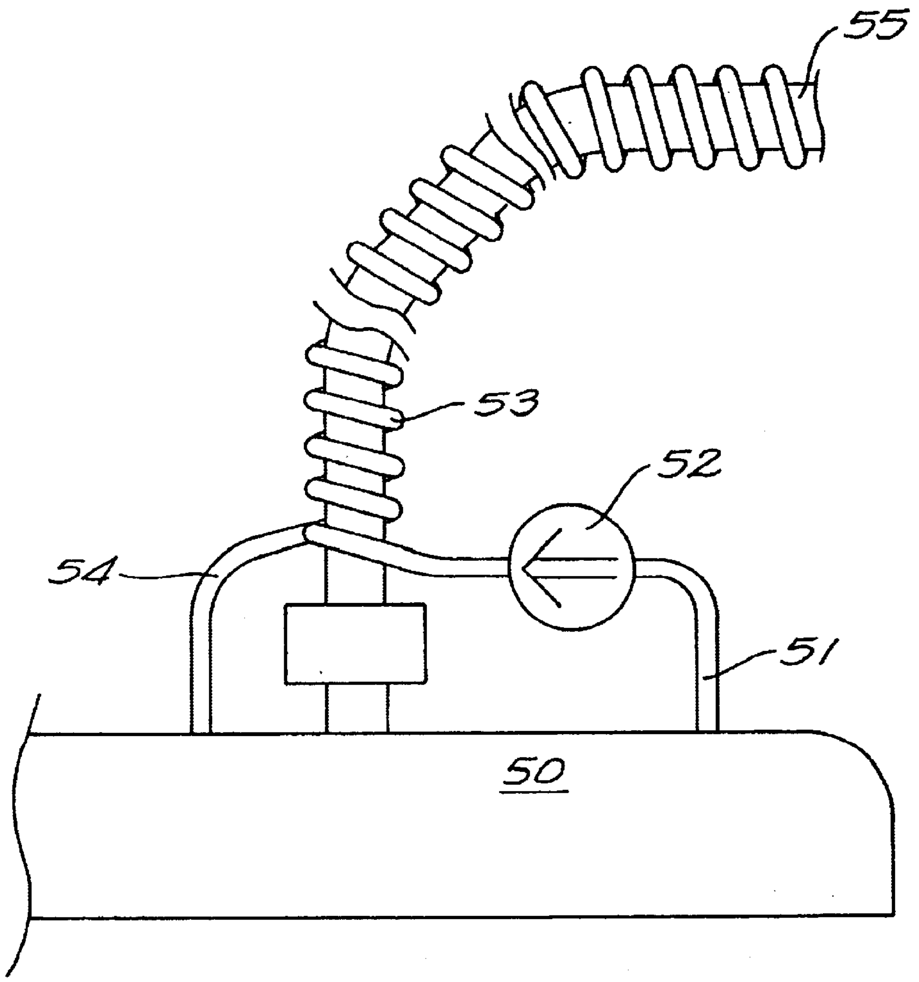

FIG. 4 operationally illustrates an embodiment of the invention which heats the hose using heat from the pressure vessel.

DRAWINGS IN DETAIL

Figure 1A:
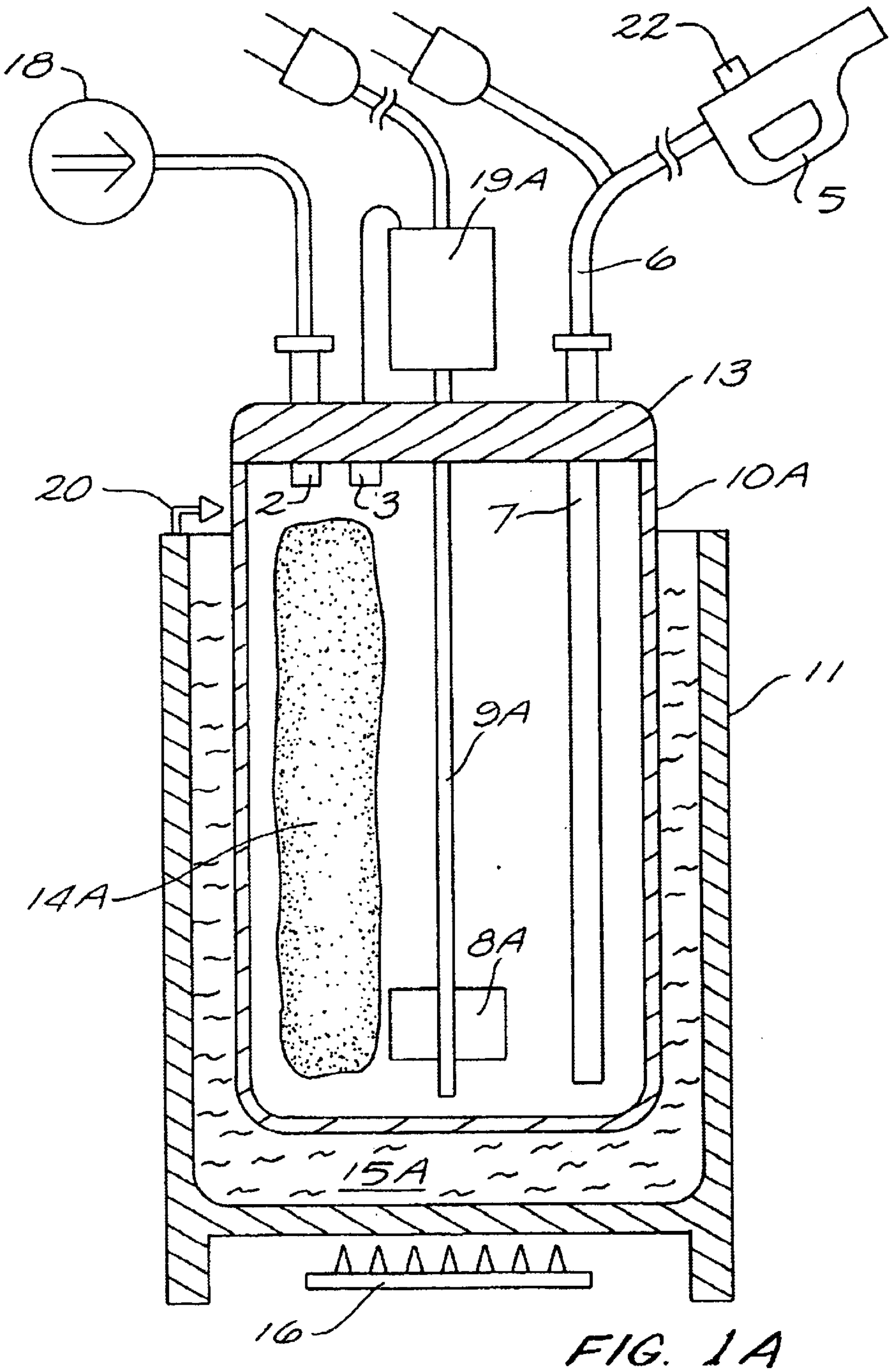
Figure 1B:
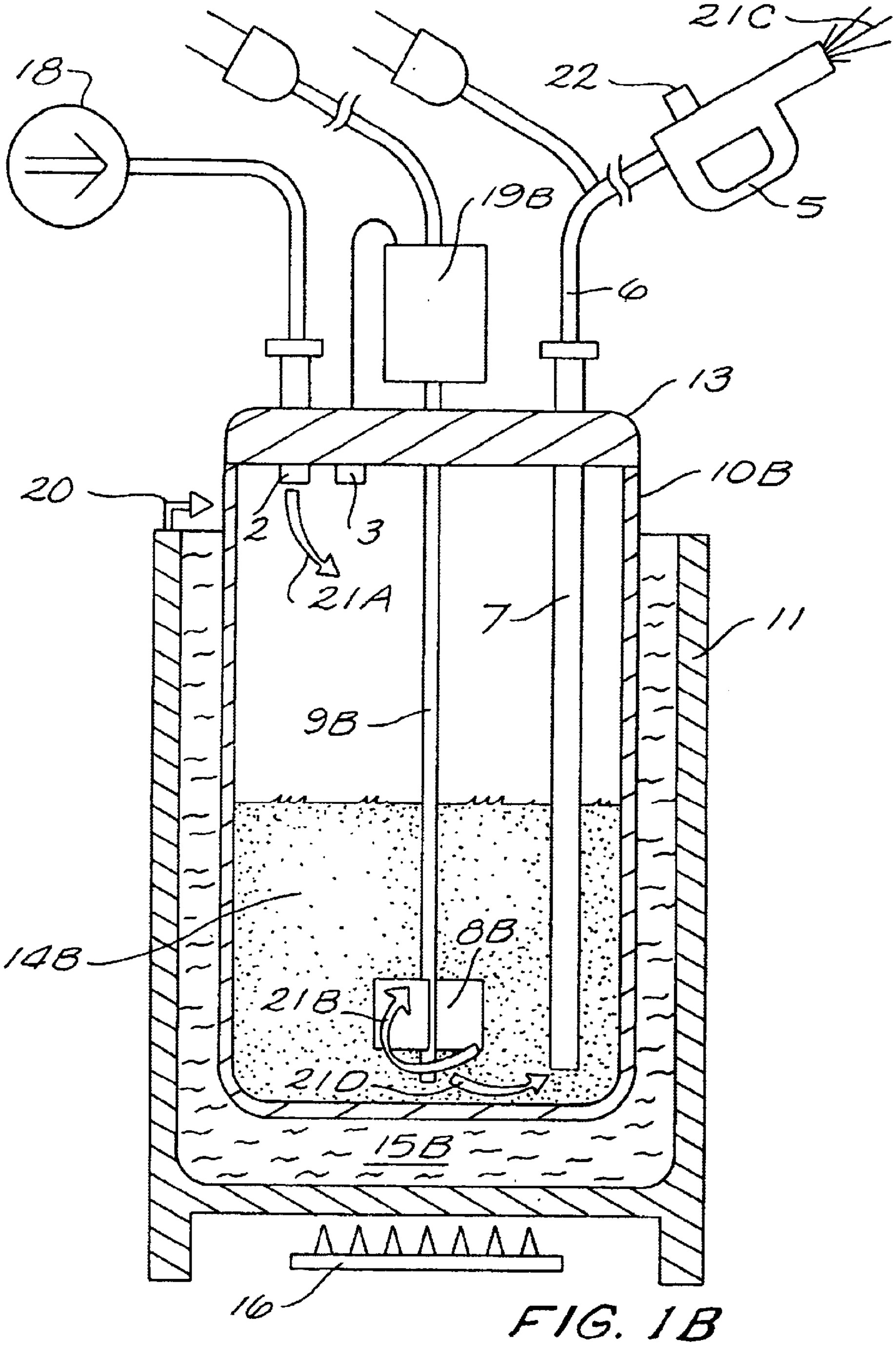

FIGS. 1A and 1B graphically illustrate the operation of the preferred embodiment of the invention.

FIG. 1A illustrates the beginning operation of the invention. A solid mass of material 14A is placed within pressure vessel 10A. Removable Hatch 13 allows the depositing of solid material 14A, removable hatch 13 is then resealed.

This material is chosen by the artist/operator, such as clay or wax. In the case of clay for material 14A, suitable clays (such as J-MAC Classic Clay-Brown and J-MAC Classic Clay-tan) are available from J.F. McCaughin Company of Rosemead, Calif.

Pressure vessel 10A is contained within heating vessel 11 and is supported/floated in a pool of water 15A. Water 15A is heated by burner 16 and is fired by propane; other sources of heating water 15A are acceptable.

The preferred pressure vessel is produced by Binks Manufacturing Company of Franklin Park, Ill. This pressure vessel is made of steel and has an internal volume of ten gallons.

During the beginning of the operation, while material 14A is still solid, motor 19A is inactive. Motor 19A is connected to stir rod 9A through removable hatch 13. At the end of sir rod 9A is paddle 8A. Motor 19A, in this embodiment, is controlled by sensor 3 which opens (deactivating motor 19A) when the temperature within pressure vessel 10A reaches a set activation point. While this activation point is chosen during the manufacture of the item in this embodiment, in some embodiments, the activation point is selectable by the operator.

In some embodiments of the invention pressure pump 18 is inactive during the heating stage, in other embodiments, pressure vessel 10A is pressurized during the heating stage. Pressure pump 18 is used to pressurize the interior of pressure vessel 10A via inlet 2.

Stand pipe 7 extends through removable hatch 13 with its open end proximate to a bottom of pressure vessel 10A. Stand pipe 7 communicates with heated hose 6 and nozzle 5. In the preferred embodiment, nozzle 5 is a Binks Mach 1SL HVLP Spray Gun commercially available from Binks Manufacturing Company. Heated hose 6 is ideally a Series 212 Teflon RFE Core Hose from Technical Heaters Inc.

Control 22 is adjusted by the operator to control the parameters of the flow through nozzle 5.

Pointer 20 is used to identify a "starting" or initial point where pressure vessel 10A is fully loaded with material 14A. Since pressure vessel 10A is floating in water 15A, fully loaded with material 14A, pressure vessel 10A will rest a certain level.

FIG. 1B illustrates-the state of the preferred embodiment once solid material 14A has been liquidified 14B.

At this point, temperature sensor 3 closes to activate electrical motor 19B so that sir rod 9B rotates at a slow speed, causing paddles 8B to mix liquid material 14B as illustrated by arrow 21B.

Pump 18 has now pressurized the interior of pressure vessel 10B as illustrated by arrow 21A. This pressure forces melted material 14B to pass into stand pipe 7 as indicated by arrow 21D.

The melted material passes through stand pipe 7 and into heated hose 6. The material is discharged, as indicated by arrows 21C, when the operator uses nozzle 5.

As the material is discharged, pressure vessel 10B and its contents becomes lighter, thereby allowing pressure vessel 10B to float higher. This difference in flotation level is noted by pointer 20 to alert the operator on when all of the material has been discharged or needs to be refreshed.

With this embodiment, the operator is able to safely melt the material and then apply it to the desired depth on the for the enlargement.

Figure 2:
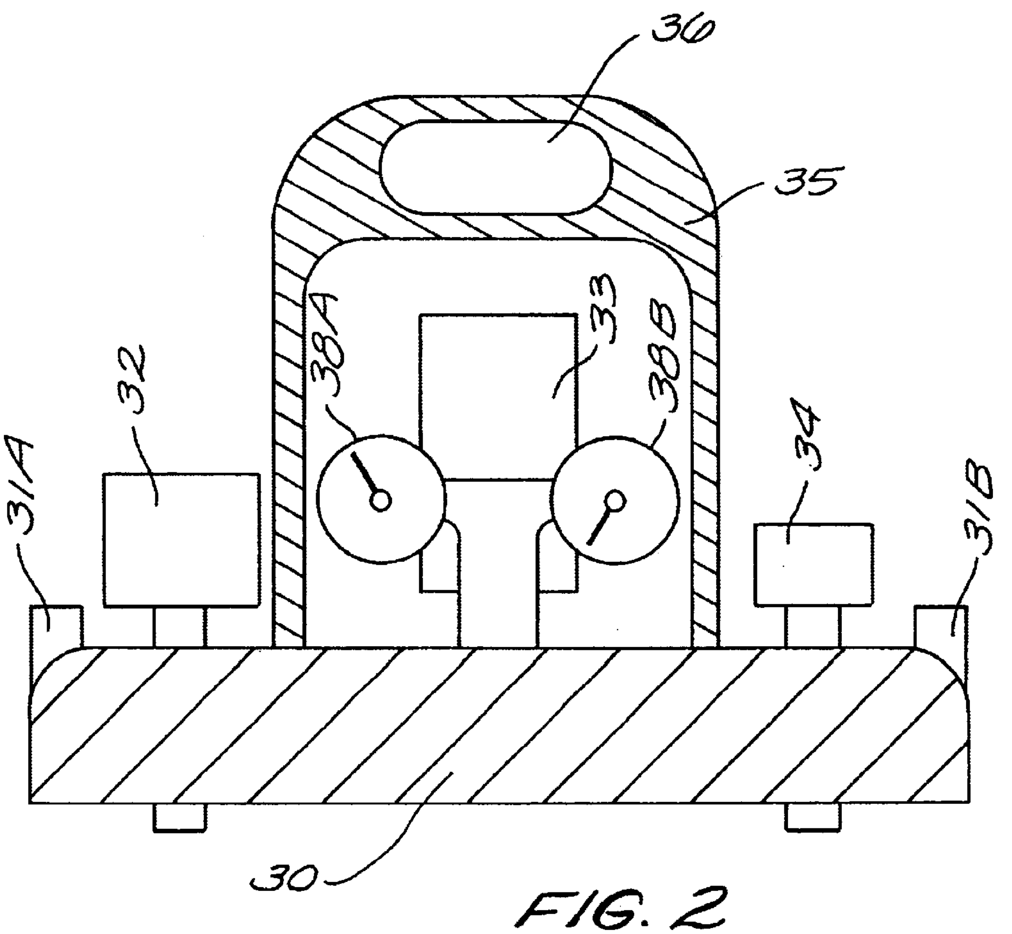
FIG. 2 illustrates an embodiment of the pressure vessel cover.

FIG. 2 illustrates an embodiment of the pressure vessel cover.

In this embodiment, removable hatch 30 includes connector seats 31A and 31B which are used to received clamps (not shown) and provide a seal between cover 30 and the underlying pressure vessel .

Pump 32 communicates with the interior portion of cover 30 and is used as outlined above to pressurize the interior of the pressure vessel.

Connector 34 is communicates with the stand pipe (not shown) and is used to connect the hose (also not shown) thereto as outlined above.

Gauges 38A and 38B are used to monitor the internal pressure (gauge 38A) and the internal temperature (gauge 38B). Each of the gauges is equipped with a trigger mechanism to shut off the corresponding mechanism when the desired pressure and temperature is met. That is, gauge 38A is used to de-activate pump 32, gauge 38B is used to de-activate siring motor 33.

Handle 35 is secured to removable hatch 30 and is used to remove removable hatch 30 from the pressure vessel. At the top of handle 35 is slot 36 through which a hook or cable is secured to assist in the removal of removable hatch 30.

Figure 3:
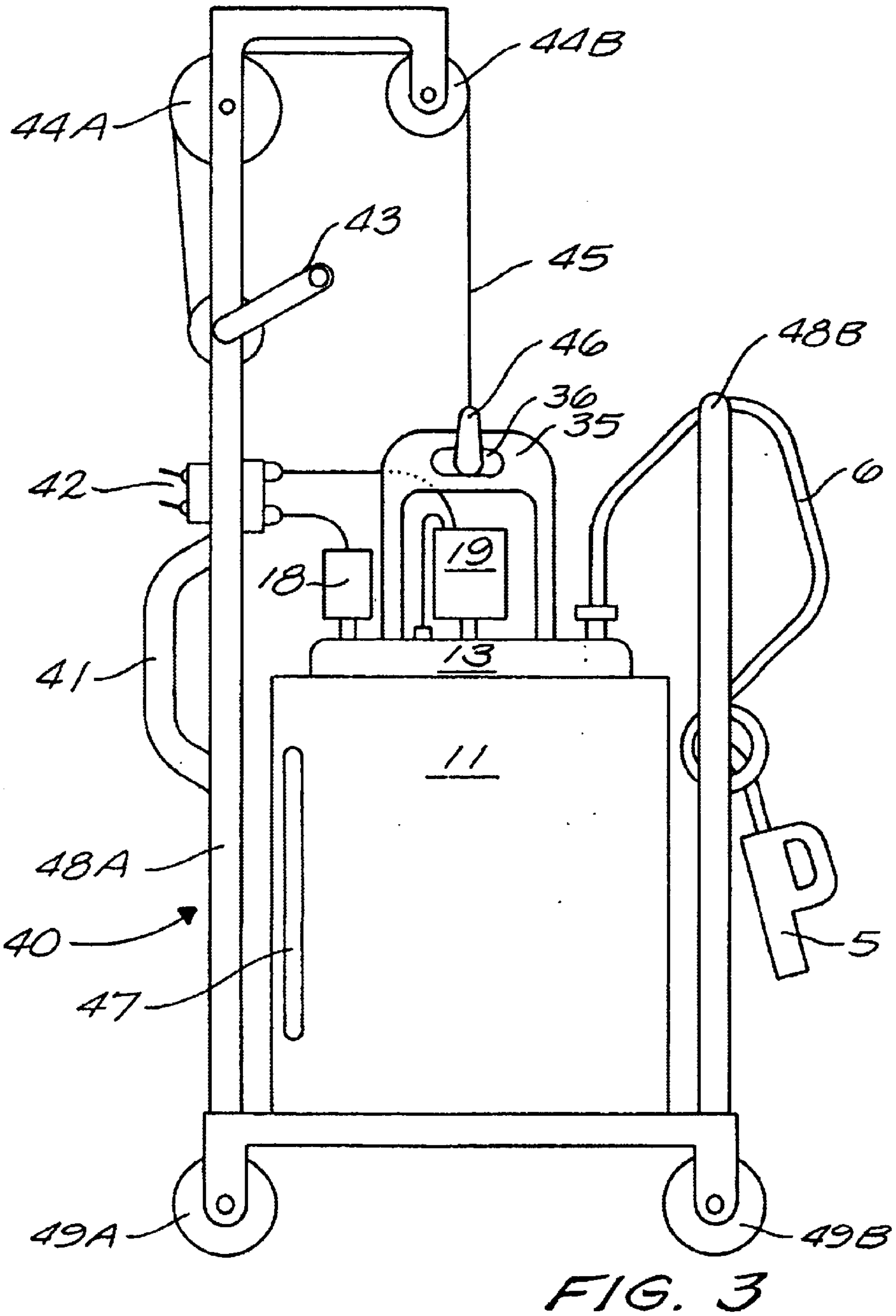
FIG. 3 illustrates the preferred embodiment mounted on a portable carnage.

FIG. 3 illustrates the preferred embodiment mounted on a portable carriage.

Carnage 40 is supported by four wheels (wheel 49A and 49B are visible from this angle, the other wheels are not). Heating vessel 11 is supported and secured to carriage 40.

Arm 48A of carriage 40A includes handle 41 which is used in transporting the assembly from point to point. Switches 42 are used to activate the pressure pump and the stirring motor 19.

Also on arm 48A is cable crank 43. A cable from cable crank 43 extends around pulley 44A and pulley 44B and is secured to slot 36 of handle 35. The operator, by using cable crank 43 is able to lift removable hatch 13 from the top of the pressure vessel (not visible in this illustration).

Arm 48B includes hooks for supporting heated hose 6 and nozzle 5 when they are not in use and for transportation.

In this embodiment of the invention, slot window 47 permits the use to monitor the level of water within heating vessel.

FIG. 4 operationally illustrates an embodiment of the invention which heats the hose using heat from the pressure vessel.

To maintain a liquid state of the material passing through hose 55, the heated atmosphere within the pressure vessel is drawn by hose 51 through removable hatch 50 by pump 52. The heated atmosphere passes around hose 55 by hose 53, thereby heating hose 55. After passing the entirety of hose 55, the atmosphere is then re-introduced into the pressure vessel via hose 54.

In this manner, heat from within the pressure vessel is used to heat the hose leading to the nozzle.

It is clear that the present invention creates a highly improved apparatus for the application of clay, wax, and other such materials.

What is claimed is:

1. An applicator for clay comprising:

a) a heating vessel having,
   1) a basin containing water, and,
   2) means for heating water within said basin to a boiling point of water;

b) a pressure vessel, at least a portion of said pressure vessel submerged within the water of said basin, said pressure vessel having,
   1) a re-sealable hatch through which clay is deposited into an interior of said pressure vessel,
   2) a pressure inlet, and,
   3) an outlet, said outlet communicating with a lower portion of the interior of said pressure vessel;

c) pressurization means communicating with said pressure inlet of said pressure vessel for pressurizing the interior of said pressure vessel to a selected pressurization;

d) a hose, a first end of said hose communicating with the outlet of said pressure vessel;

e) a spray nozzle, said spray nozzle being selectively operated by a user, said nozzle secured to a second end of said hose;

f) means for heating said hose and said spray nozzle; and g) means for alerting an operator by flotation of said pressure vessel within said heating vessel.

2. The applicator for clay according to claim 1, further including a paddle mounted within said pressure vessel, said paddle, when rotating, mixing a liquidified clay therein.

3. The applicator for clay according to claim 2, wherein said paddle is powered by an electric motor.

4. The applicator for clay according to claim 3, further including a temperature probe having means for activating said electric motor when a temperature within said pressure vessel reaches a selected level.

5. The applicator for clay according to claim 4, wherein said selected level is established by an operator.

6. The applicator for clay according to claim 1, further including a frame supporting said heating vessel, the pressure vessel, said hose, said spray nozzle, and said means for heating.

7. The applicator for clay according to claim 6, further including a wheeled carriage supporting said frame.

8. The applicator for clay according to claim 7, further including means for lifting said re-sealable hatch of said pressure vessel, said means for lifting being supported by said frame.

9. The applicator for clay according to claim 1, further including means for alerting an operator if a level of water within said heating vessel falls to a selected level.

10. The clay applicator according to claim 9, wherein said means for alerting an operator includes a visual readout of a level of said water.

11. The applicator for clay according to claim 1, wherein said pressurization means also communicates air pressure to said spray nozzle.

12. The applicator for clay according to claim 11, wherein said spray nozzle includes means for adjusting an air pressure passing through said spray nozzle.

13. An apparatus for an artist comprising:

a) a heating vessel having boiling water therein;

b) a pressure vessel at least partially submerged within the boiling water of said heating vessel, said pressure vessel having a chosen material therein;

c) pressurization means for pressurizing an interior of said pressure vessel;

d) a hose, a first end thereof communicating with an interior of said pressure vessel, said hose having a spray nozzle on a second end thereof; and, e) means for alerting an operator by flotation of said pressure vessel within said heating vessel.

14. The apparatus according to claim 13, further including means for heating said hose.

15. The apparatus according to claim 14, wherein said means for heating includes means for circulating heated air from an interior of said pressure vessel around an exterior of said hose.

16. The apparatus according to claim 13, wherein said heating basin includes:

a) a vessel containing water; and, b) means for heating water within said vessel to a boiling point.

17. The apparatus according to claim 13, wherein said pressure vessel includes a re-sealable hatch through which said chosen material is deposited into an interior of said pressure vessel.

18. The apparatus according to claim 13, further including a frame supporting said heating vessel, the pressure vessel, said hose, said spray nozzle, and said means for heating, said frame having:

a) a wheeled carriage supporting said frame; and, b) means for lifting said re-sealable hatch of said pressure vessel.

19. An artist apparatus comprising:

a) a heating vessel containing boiling water;

b) a sealed pressure vessel having a solid material therein, said sealed pressure vessel being partially submerged in said boiling water;

c) pressurization means for maintaining pressure within said sealed pressure vessel, above ambient pressure;

d) a hose, a first end of said hose communicating with an interior of said pressure vessel;

e) a spray nozzle, said spray nozzle being selectively opened by a user, said nozzle secured to a second end of said hoses; and, f) means for alerting an operator by flotation of said pressure vessel within said heating vessel.

20. The artist apparatus according to claim 19, further including a paddle activated when said solid material within said pressure vessel becomes liquidified.

* * * * *